United States Patent [19]

Reininghaus

[11] 3,976,053

[45] Aug. 24, 1976

[54] APPARATUS AND METHODS FOR USE IN MEASURING RESPIRATION CHARACTERISTICS

[75] Inventor: Wolf Reininghaus, Cologne, Germany

[73] Assignee: Philip Morris Incorporated, New York, N.Y.

[22] Filed: May 27, 1975

[21] Appl. No.: 581,101

[52] U.S. Cl. .............................................. 128/2.08
[51] Int. Cl.² .......................................... A61B 5/08
[58] Field of Search ................ 128/2.07, 2.08, 30.2, 128/142.5

[56] References Cited
UNITED STATES PATENTS

| | | | |
|---|---|---|---|
| 2,569,849 | 10/1951 | Emerson | 128/2.08 |
| 3,324,848 | 6/1967 | Domeier | 128/2.08 |
| 3,401,683 | 9/1968 | Webb | 128/2.07 |
| 3,730,173 | 5/1973 | Deaton | 128/2.08 |
| 3,913,379 | 10/1975 | Rusz | 128/2.08 X |

Primary Examiner—Harland S. Skogquist
Attorney, Agent, or Firm—Watson Leavenworth Kelton & Taggart

[57] ABSTRACT

Laboratory research animals or like subjects are disposed together with a fluid medium in a vessel supporting the head portion of the animal in isolation from the fluid medium and exposed to a separate environment. Fluid medium flow occasioned by movements of the animal body portion in engagement with the fluid medium are detected and processed to provide information regarding respiration characteristics of the animal.

11 Claims, 4 Drawing Figures

APPARATUS AND METHODS FOR USE IN MEASURING RESPIRATION CHARACTERISTICS

FIELD OF THE INVENTION

This invention pertains to apparatus and methods for use in measuring respiration characteristics of a subject.

SUMMARY OF THE INVENTION

Methods in accordance with the invention contemplate selectively confining, in a volume containing a fluid medium, a body portion of a subject which is displaced during respiration and, while disposing a further body portion of the subject inclusive of its respiratory organs exteriorly of and sealably separate from fluid medium encircling the subject in such volume, measuring movement of such fluid medium occasioned by respiratory activity of the subject.

Apparatus according with the invention comprises a vessel for containing, together with a fluid medium, a portion of a subject displaced during respiration and having an opening for sealably encircling such as the neck portion of the subject, thus disposing the head of the subject exteriorly of and sealably separate from fluid medium encircling the subject in the vessel. A conduit supporting substantially free fluid medium flow is arranged in sealed engagement with a further opening in the vessel and a sensing element is disposed in the conduit for generating a signal indicative of fluid medium flow therethrough. In its preferred embodiment, the sensing element has electrical resistance variable both in accordance with fluid flow in the conduit and with electrical voltage applied thereacross. Circuitry is included for detecting changes in electrical resistance of the sensing element due to fluid medium flow. Other circuitry applies voltage to the sensing element and is responsive to the aforementioned circuitry to compensatingly change the voltage applied thereby to the sensing device whereby the electrical resistance of the sensing element is maintained at a preselected resistance value. The voltage changing activity of the latter circuitry is processed by further circuitry to generate output signals indicative of the frequency of respiration, the volume of respiration and the mean respiration volume per unit time.

The invention will be more fully understood by a consideration of the following detailed description of preferred methods and embodiments of the invention and from the drawings thereof wherein like reference numerals are used to identify like parts throughout.

DETAILED DESCRIPTION OF THE PREFERRED EMBODIMENT

Figure 1:
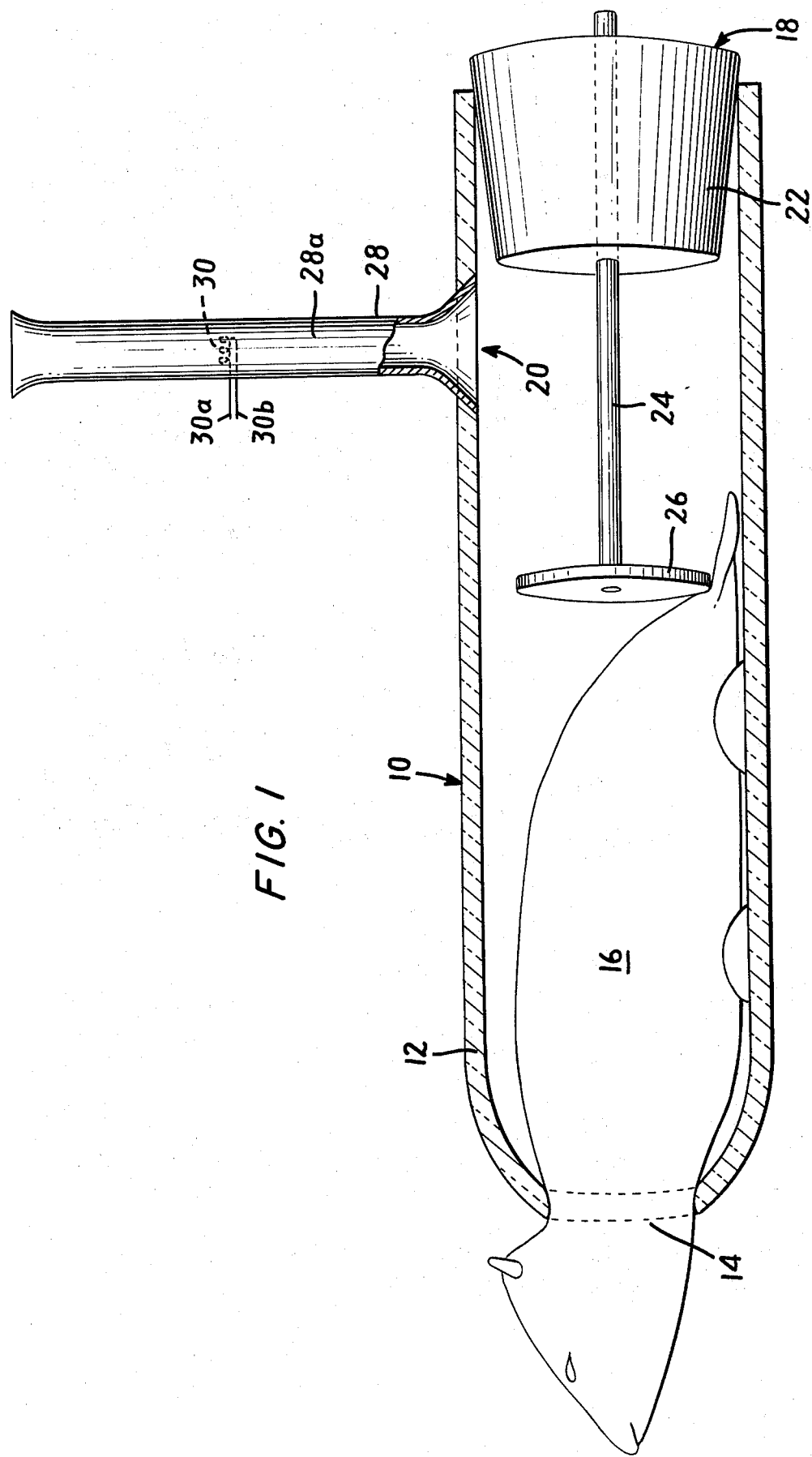
FIG. 1 shows a vessel together with subject movement confining and fluid medium flow sensing accessory apparatus.

Referring to FIG. 1, elongate vessel 10 includes a wall 12 defining a frontal opening 14 adapted to sealably encircle generally the neck portion of subject 16, a rearward opening 18 through which the subject may be placed within the vessel, and an upper opening 20. The wall portion defining opening 18 is sealably closed by plug 22 which is adapted to sealably support plunger 24 for adjustable longitudinal positioning in the vessel whereby disc member 26, secured to the interior end of the plunger, may engage the subject and limit its movement rightwardly in FIG. 1. The wall portion defining opening 20 is sealably engaged by the lower end of a conduit-defining pipe 28, the conduit 28a having a lower opening in facing relation to opening 20. Between its lower end and its upper end, pipe 28 supports a sensing element or probe 30 therein having leads 30a and 30b. The sensing element is preferably of the type employed in hot wire anemometry, e.g., an element having electrical resistance variable in accordance both with cooling thereof by movement of fluid medium, i.e., a gas, in conduit 28a and with electrical voltage applied across leads 30a and 30b. As is discussed more fully below, the voltage applied to the sensing element is regulated to compensate for resistance change due to fluid medium flow whereby the sensing element resistance is effectively maintained constant, i.e., at a preselected value. Changes in voltage applied to the sensing element are employed in accordance with the invention to provide indications of various respiration parameters, e.g., respiration frequency, net respiration volume and mean respiration volume per unit time.

Figure 2:
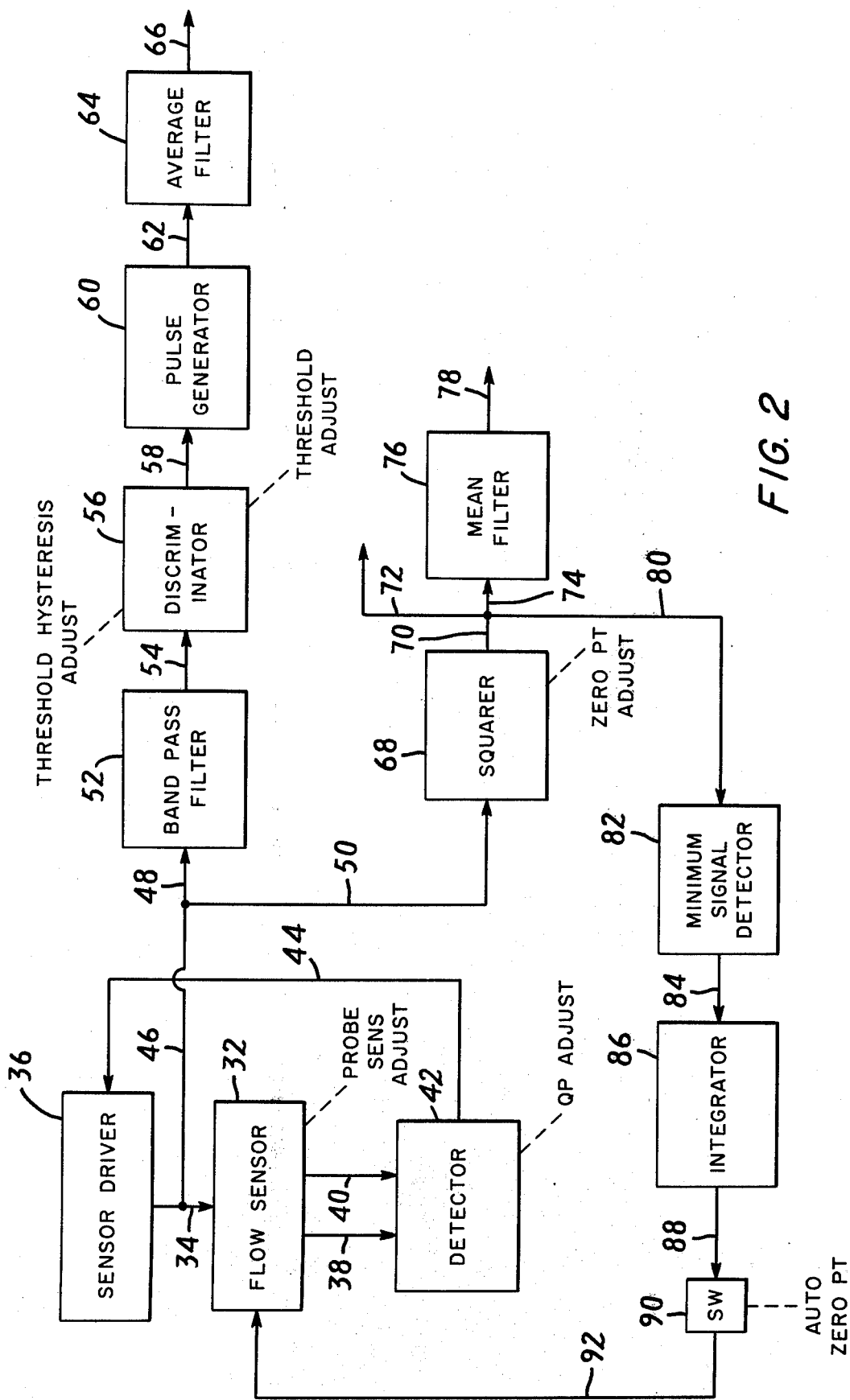
FIG. 2 is a functional block diagram of a respiratory activity determining system according with the invention.

Referring now to FIG. 2, flow sensor 32 includes sensing element 30 and receives voltage on line 34 from sensor driver 36. Flow sensor 32 provides output signals indicative of voltage change across sensing element 30 thereof on lines 38 and 40 which lead to detector 42. Unit 42 generates on line 44 an output signal, indicative of such voltage change (resistance change of sensing element 30), and applies the same to sensor driver 36 which is responsive to such unit 42 output signal to vary the voltage it supplies on line 34 to flow sensor 32.

Line 46 conveys the line 34 signal to lines 48 and 50, the former leading to bandpass filter 52, which passes lines 34 signals of preselected frequency to line 54 and thence to discriminator 56. Unit 56 provides an output signal on line 58 for each line 54 signal applied thereto in excess of a predetermined voltage level. Pulse generator 60 generates, for such line 58 signals, output pulses on line 62 each of like amplitude and time extent. Line 62 applies such pulses to average filter 64 which generates an output signal on line 66 having an amplitude level equal to the average value of the line 62 pulses.

Since resistance change in sensing element 30 is caused, apart from compensating resistance change brought about by sensor driver 36, by the effect on the sensing element of fluid medium flow in the conduit 28a, the line 34 signal exhibits change according with fluid medium flow and by processing of the line 34 signal in units 52, 56, 60 and 64, the line 66 signal is indicative of respiration frequency.

Line 50 conveys the line 34 signals to squarer 68, effectively performing a linearization of the flow-voltage relationship, therefore providing a flow proportional output signal on line 70. Line 70 is connected to line 72 and provides output signals indicative of the results of such signal squaring, i.e., respiration volume.

The line 70 signal is applied also to line 74 and thence to mean filter 76 which generates on line 78 an output signal indicative of the mean value of the line 70 signal per unit time, i.e., mean respiration volume per unit time.

Unit 82 looks to the signal applied thereto on line 80, in turn connected to line 70, to determine the minimum amplitude value thereof. Such minimum value, which occurs during the pause between inhalation and exhalation by the subject, is a measure of drift in the apparatus and the apparatus is desirably corrected such that output indications may be essentially drift-free. Unit 82 applies its output signal to line 84 which leads to integrator 86 which performs long term integration of the drift-indicative signal and applies the result of such integration to line 88 and through switch 90 and line 92 to flow sensor 32 whereby a drift-corrective voltage is furnished to the flow sensor.

Figures 3, 4:
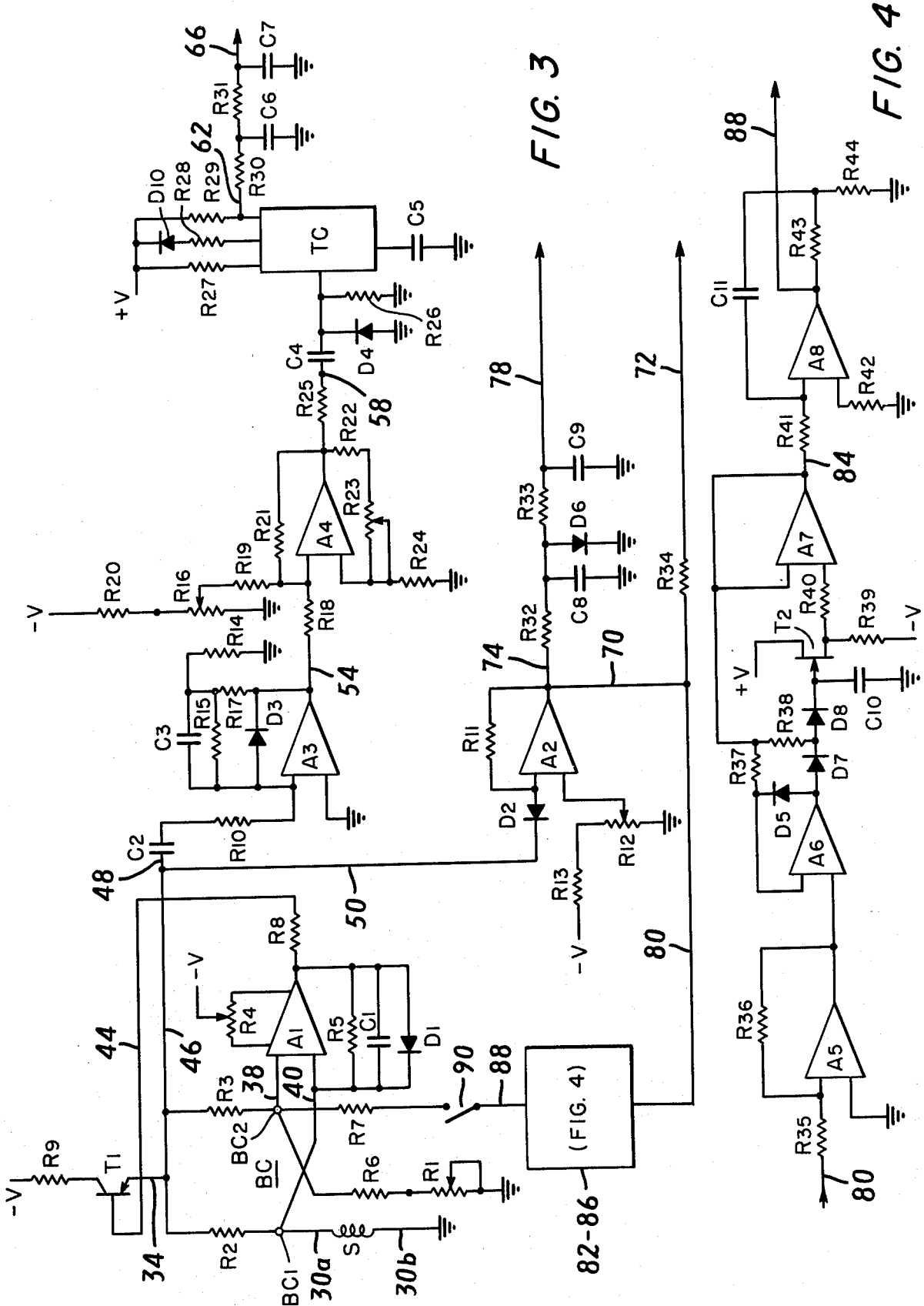
FIG. 3 is a detailed diagram, partly in block and partly schematic, of circuitry for implementing the FIG. 2 system.
FIG. 4 is a detailed schematic diagram of the circuitry shown in block form in FIG. 3.

Referring now to FIG. 2 together with FIG. 3, flow sensor 32 of FIG. 2 is constituted by a bridge circuit BC having a first branch including probe S (element 30 of FIG. 1) in series circuit with resistor R2 and a second branch including resistors R1 and R6 in series circuit with resistor R3. The bridge is itself series connected between line 34 and ground, with line 34 connected to a single stage (constituting sensor driver 36 of FIG. 2) comprising transistor T1 and resistor R9. Resistor R9 is connected between a negative voltage (−V) and the collector of transistor T1. The transistor T1 emitter is connected to line 34 and the transistor T1 base is connected to line 44.

The respective junctions BC1 and BC2 of the first and second branches of bridge circuit BC are separately connected by lines 38 and 40 to the input terminals of circuitry constituting detector 42 of FIG. 2 and comprising amplifier A1, resistors R4, R5 and R8, capacitor C1 and diode D1.

In operation of the circuitry discussed to this juncture, on the occurrence of voltage differences between lines 38 and 40, caused by changes in the resistance of probe S due to flow of fluid medium thereacross, amplifier A1 applies a signal to line 44 indicative of such voltage differences and effective to vary conduction in transistor T1 and accordingly to vary the voltage applied to the bridge circuit. By way of example, where probe S is cooled by fluid medium flow, its resistance decreases whereby the line 40 voltage goes more positive than the line 38 voltage, giving rise to a voltage difference between lines 38 and 40. Amplifier A1 is responsive to such voltage difference to drive the voltage applied to line 44 more negative whereby current flow in transistor T1 is increased resulting in an increased current flow and an increased heat loss in the bridge circuit. The circuitry under consideration defining a closed loop, such current increasing continues until the preselected temperature and resistance of probe S are regained and by this means the voltage difference between lines 38 and 40 is driven to zero.

Line 46 applies to lines 48 and 50 the signal applied by line 34 to bridge circuit BC. Line 48 leads to circuitry constituting bandpass filter 52 of FIG. 2 comprising amplifier A3, resistors R10, R14, R15 and R17, capacitors C2 and C3 and diode D3. The lower limit frequency defined by such active filter circuit may be approximately 0.24 hertz and the upper limit approximately 3.0 hertz.

Amplifier A3 drives line 54 of FIG. 2, thus applying the filter 52 output signals to circuitry constituting discriminator 56 of FIG. 2 comprising amplifier A4, resistors R16 and R18 through R25. By appropriately setting resistor R16, the threshold level of the discriminator is adjusted such that it generates output pulses on line 58 upon each occurrence of signals of preselected voltage level on line 54. By appropriately setting resistor R23, the hysteresis between "on" and "off" threshold level of the discriminator is adjusted such that multiple triggering on disturbed signals is prevented.

The line 58 pulses are applied to circuitry constituting pulse generator 60 of FIG. 2 comprising timing circuit TC, resistors R26 through R29, capacitor C5 and diodes D4 and D10, resistors R27 and R29 and diode D10 being connected to a positive potential +V. The pulse generator output on line 62 is applied to circuitry constituting average filter 64 of FIG. 1 comprising resistors R30 and R31 and capacitors C6 and C7 and thence to apparatus output line 66.

The line 50 signal is applied to circuitry constituting squarer 68 of FIG. 2 comprising amplifier A2, resistors R11 through R13 and diode D2. The squared output signals on line 70 are applied through resistor R34 to apparatus output line 72 and are further applied through line 74 to circuitry constituting mean filter 76 of FIG. 2 comprising resistors R32 and R33, capacitors C8 and C9 and diode D6 which applies the resulting filtered signal to apparatus output line 78.

In implementing the above-discussed drift correction, bridge circuit BC includes a resistor R7 connected to junction BC2 and further connected to a terminal of switch 90. The preferred circuitry interconnecting the remaining terminal of switch 90 (line 88) to line 80 is shown in FIG. 4, to which reference is now made. Minimum signal detector 82 of FIGS. 2 and 3 is implemented in FIG. 4 by circuitry including a first stage connected to line 80 and comprising amplifier A5 and resistors R35 and R36, a second stage including amplifier A6, resistors R37 and R38, diodes D5, D7 and D8 and capacitor C10, a third stage incorporating field-effect transistor T2 and resistor R39, and a fourth stage comprising amplifier A7 driving line 84 and resistor R40. Line 84 leads to integrator 86 of FIGS. 2 and 3 which is implemented in FIG. 4 by circuitry comprising amplifier A8, resistors R41 through R44 and capacitor C11, amplifier A8 driving line 88.

As will be appreciated, line 88 is connected by switch 90 only to one of the bridge circuit branches, as contrasted with common connection of line 34 to both bridge circuit branches. Referring to FIG. 3, switch 90 furnishes the line 88 signal to resistor R7 and thereby to junction BC2, whereby the bridge circuit is compensated for slow drifts of parameters, such as the temperature of the fluid medium.

In brief summary of the operation of the system thus described, movements of a body portion subject to displacement during respiration give rise to movement of fluid medium, in turn giving rise directly to resistance change in the sensing element from a preselected resistance. The sensing element resistance is returned from such changed value to the preselected value by controlled variation of the voltage applied to the sensing element. The periodicity of predetermined cyclic change in these voltage variations is detected to provide indication of respiration frequency. The square of such variations is determined to provide indication of respiration volume. Finally, the respiration volume is defined on a per unit time basis.

In a typical application, the apparatus of the invention is employed in measuring respiratory activity of a research animal, such as a rat. In such specific application, the subject body weight is approximately 200 grams, the respiration volume per unit time is in the vicinity of 75 milliliters per minute and respiration frequency is approximately 1 hertz. The animal itself generally provides sufficient sealing of the vessel. On the other hand, measurement accuracy may be increased by sealing the vessel opening through which the head of the animal projects by a rubber collar, such as a latex membrane 0.2 to 0.3 millimeters in thickness. Pipe 28 desirably comprises a metal tube whose internal diameter is selected for different kinds of animals such that the quotient of the double average respiratory volume per minute and the pipe cross-section results in an average air velocity of approximately 400 centimeters per minute, giving a maximal Reynold-index of about 200. The length of the pipe should be approximately twenty times its internal diameter.

The sensing element is centrally mounted in the middle of the pipe. By way of example, a 2 millimeter length tungsten coil having a wire diameter of 26 micrometers and a wire length of about 10 millimeters is stretched transversely of the tube longitudinal axis by opposed iron wires of diameter 0.3 millimeter. The sensing element is connected to the bridge circuitry by a coaxial cable.

As will be appreciated, the apparatus above-described may be employed either with or without drift correction by operator choice in setting switch 90. In preparing the apparatus for use, with switch 90 open and the probe hermetically sealed and +V at +15v and −V at −15v, the quiescent point of operation (QP) of detector 42 is adjusted. In this operation, resistor R4 of FIG. 3 is adjusted to provide a negative voltage at the output of amplifier A1. Next, probe sensitivity is adjusted with the probe sealed and at a temperature of 20°C., by varying resistor R1 of FIG. 3, until the emitter voltage of transistor T1 is at −2v. For higher sensitivity, the emitter voltage may be made more negative. With switch 90 still open, the zero point of the input signal to minimum signal detector 82 is set by adjusting resistor R12 such that line 70 voltage is zero, again with the probe sealed and probe temperature at 20°C.

To calibrate the apparatus in volume, switch 90 also remains open and a constant air stream is drawn through pipe 28 at a constant temperature. The flow rate of the air stream is measured with a flow meter and the output voltage on lines 78 and 72 is observed. Since the sensing element sees both inhaled and exhaled air quantity, the volume per minute value indicated by the flow meter is divided by a factor of two to correctly correlate the measured voltages with actual respiratory volume.

The threshold adjustment to discriminator 56 of FIG. 2 is made with the subject disposed in the vessel by adjusting resistor R16 (FIG. 3) until light-emitting diode D10 is illuminated once during each respiratory cycle.

In implementing the circuitry of FIGS. 3 and 4, amplifiers A1 through A8 may comprise Siemens operational amplifiers TBA221. Timing circuit TC may comprise an EXAR timing circuit XR320 with terminals 7 and 14 connected to +15v, terminal 1 connected to R27, terminal 3 connected to C5, terminal 5 connected to R26, C4 and D4, terminals 6 and 8 grounded, terminal 10 connected to R29 and R30 and terminal 12 connected to R28. Diodes D1 and D3 through D9 may comprise silicon diodes 1N914. Diode D2 may be a Valvo germanium point contact diode AA119. Diode D10 may be a light-emitting diode OLD415. Transistor T1 may be a Valvo transistor BC161-16. Transistor T2 may be a Solidev field-effect transistor 2N3687. The values of the resistors and capacitors of the apparatus are listed in Table 1 below, respectively in kilohms and microfarads.

Table 1

| | |
|---|---|
| C1, C4, C10 | .100 |
| C2 | 1.5 |
| C3 | .470 |
| C5 | .047 |
| C6, C7, C8, C9 | 100 |
| C11 | 10 |
| R1 | .1 |
| R2 | .02 |
| R3 | 17.5 |
| R4 | 10 |
| R5 | 100 |
| R6 | .91 |
| R7 | 1000 |
| R8 | 1000 |
| R9 | .083 |
| R10 | 100 |
| R11 | .390 |
| R12 | 5 |
| R13 | 10 |
| R14 | 1 |
| R15 | 510 |
| R16 | 5 |
| R17 | 20 |
| R18 | 5.1 |
| R19 | 10 |
| R20 | 10 |
| R21 | 2000 |
| R22 | 12 |
| R23 | 100 |
| R24 | .390 |
| R25 | 100 |
| R26 | 10 |
| R27 | 620 |
| R28 | .510 |
| R29 | 2 |
| R30 | 10 |
| R31 | 10 |
| R32 | 10 |
| R33 | 10 |
| R34 | (1 to 10) |
| R35 | 18 |
| R36 | 10 |
| R37 | 20 |
| R38 | 1000 |
| R39 | 18 |
| R40 | 20 |
| R41 | 100 |
| R42 | 1 |
| R43 | 1 |
| R44 | 10 |

Various changes and modifications now evident to those skilled in the art may readily be introduced in the foregoing functional and detailed descriptions of the invention without departing from the spirit and scope of the claims. Thus, the particularly disclosed embodiment above is intended in an illustrative and not in a limiting sense. The true spirit and scope of the invention is defined in the following claims.

What is claimed is:

1. Apparatus for use in measuring respiration characteristics of a subject, comprising:
   a. vessel means for containing a fluid medium and a subject first body portion which body portion is expansible and contractible during respiration, said vessel means having a first wall part defining an opening for sealably encircling a second body portion of such subject whereby the head portion of such subject is disposed exteriorly of said vessel means, said vessel means having a second wall part defining a further opening;
b. conduit means having a first end in sealable engagement with said vessel means second wall part defining said further opening and having a second end and supporting substantially free fluid medium flow between said first and second ends thereof; and
c. sensor means disposed in said conduit means for generating an output signal indicative of fluid medium flow between said conduit means first and second ends and thus indicating displacement of said subject first body portion.

2. The apparatus claimed in claim 1 further including means adjustably positionable in said vessel means for engaging a subject therein to limit movement of such subject.

3. The apparatus claimed in claim 1 wherein said sensor means comprises a sensing element having preselected electrical resistance variable both in accordance with fluid medium flow in said conduit means and in accordance with electrical voltage across said element.

4. The apparatus claimed in claim 3 further including first circuit means for generating output signals indicative of changes in the electrical resistance of said sensing element from said preselected resistance and second circuit means for applying voltage across said sensing element and responsive to said first circuit means output signals to vary such applied voltage to return said sensing element resistance from such changed resistance to said preselected resistance.

5. The apparatus claimed in claim 4 further including third circuit means responsive to such variations in said voltage applied across said sensing element for generating an output signal indicative of the periodicity of pedetermined cyclic change in said variations in said applied voltage and thereby indicative of the respiration frequency of said subject.

6. The apparatus claimed in claim 5 further including fourth circuit means responsive to such variations in said voltage applied across said sensing element for generating an output signal indicative of the square of said variations and thereby indicative of the respiration volume of said subject.

7. The apparatus claimed in claim 6 further including fifth circuit means responsive to the output signal of said fourth circuit means for generating an output signal indicative of the mean volume indicated therein per unit time.

8. The apparatus claimed in claim 3 wherein said sensing element is connected in a first branch of a bridge circuit also including a second branch, said apparatus further including a first circuit for generating an output signal indicative of voltage difference between said first and second bridge branches, a second circuit responsive to said first circuit output signal to supply a common voltage to both said bridge circuit first and second branches for maintaining said sensing element at a preselected resistance value and a third circuit including an integrator responsive to said first circuit output signal to supply a further voltage to said bridge circuit second branch.

9. A method for determining respiration characteristics of a subject comprising the steps of:
a. confining a first body portion of said subject which body portion is expansible and contractible during respiration within a volume also containing a fluid medium;
b. disposing the head portion of said subject exteriorly of said volume; and
c. measuring fluid medium movement in said volume.

10. The method claimed in claim 9 including the further step of engaging said subject in a manner limiting its mobility in said volume.

11. The method claimed in claim 9 wherein said volume is defined by a vessel having an opening and including the step of forcing into said vessel opening a further body portion of said subject joining said subject first body portion and the head portion of said subject.

* * * * *